(12) United States Patent
Wittendorff et al.

(10) Patent No.: US 11,541,217 B2
(45) Date of Patent: Jan. 3, 2023

(54) TATTOOING APPARATUS

(71) Applicant: Wit Innovation ApS, Roskilde (DK)

(72) Inventors: Klaus Kristoffer Wittendorff, Roskilde (DK); Asmundur Marteinsson, Copenhagen (DK)

(73) Assignee: Wit Innovation ApS, Roskilde (DK)

( * ) Notice: Subject to any disclaimer, the term of this patent is extended or adjusted under 35 U.S.C. 154(b) by 298 days.

(21) Appl. No.: 16/763,381

(22) PCT Filed: Nov. 15, 2018

(86) PCT No.: PCT/EP2018/081443
§ 371 (c)(1),
(2) Date: May 12, 2020

(87) PCT Pub. No.: WO2019/096936
PCT Pub. Date: May 23, 2019

(65) Prior Publication Data
US 2020/0398036 A1    Dec. 24, 2020

(30) Foreign Application Priority Data
Nov. 15, 2017 (DK) .......................... PA 2017 70863

(51) Int. Cl.
*H02H 3/00* (2006.01)
*A61M 37/00* (2006.01)

(52) U.S. Cl.
CPC ..... *A61M 37/0076* (2013.01); *A61M 2205/33* (2013.01)

(58) Field of Classification Search
None
See application file for complete search history.

(56) References Cited

U.S. PATENT DOCUMENTS

| 4,751,437 A | * | 6/1988 | Gerard | H01J 23/20 |
| | | | | 318/135 |
| 2002/0093302 A1 | * | 7/2002 | Rich | G05B 19/237 |
| | | | | 318/459 |
| 2005/0277973 A1 | | 12/2005 | Huang et al. | |
| 2017/0007814 A1 | | 1/2017 | Chan et al. | |
| 2020/0268362 A1 | * | 8/2020 | Van Liere | A61B 10/0266 |

FOREIGN PATENT DOCUMENTS

| CN | 105381535 A | 3/2016 |
| DE | 102008031907 A1 | 1/2010 |
| WO | WO-2015/156715 A1 | 10/2015 |
| WO | WO-2016/109746 A2 | 7/2016 |

OTHER PUBLICATIONS

International Search Report from PCT/EP2018/081443, dated Mar. 11, 2019.

* cited by examiner

*Primary Examiner* — Stephen W Jackson
(74) *Attorney, Agent, or Firm* — Morse, Barnes-Brown & Pendleton, P.C.; Sean D. Detweiler, Esq.

(57) ABSTRACT

An oscillating apparatus, such as a tattooing apparatus applying an electric motor such as a linear motor, and a first sensor and a controller. A method for controlling an oscillating apparatus such as a tattooing apparatus, includes a controller and various sensors to control, among other things, the position, velocity and acceleration of a needle either directly or via a needle connector.

16 Claims, 2 Drawing Sheets

TATTOOING APPARATUS

RELATED APPLICATIONS

This application is a national stage filing under 35 U.S.C. 371 of International Application No. PCT/EP2018/081443, filed Nov. 15, 2018, which claims priority to Denmark Application No. PA 2017 70863, Nov. 15, 2017. The entire teachings of International Application No. PCT/EP2018/081443, filed Nov. 15, 2018, are incorporated by reference herein.

FIELD OF THE INVENTION

The invention relates to an oscillating apparatus, such as a tattooing apparatus applying an electric motor such as a linear motor. Also, the invention relates to a method for controlling an oscillating apparatus such as a tattooing apparatus, comprising a controller and various sensors to control, among other things, the position, velocity and acceleration of a needle either directly or via a needle connector.

BACKGROUND

Handpoking is a very old method of applying a tattoo. The artist uses a needle attached to a pen sized stick. The needle is dipped in ink and then pressed under the skin, leaving behind a dot of ink deposited under the skin. This is essentially the whole function of a tattooing apparatus.

Today, different motors are traditionally used for driving the needle in a tattooing apparatus:

- an electromagnetic coil machine includes electromagnetic coils providing the oscillation or reciprocation of the needle. Electromagnetic coils are mounted to a frame which includes a spring-loaded armature biased away from the electromagnetic coils and the frame further includes a contact screw and an electrical contact. In operation, when the screw contacts the electrical contact, then the electromagnetic coils receive power and create a magnetic field which attracts the armature towards the electromagnetic coils. As the armature moves toward the electromagnetic coils, the armature drives the needle into the skin. Further, as the armature moves towards the electromagnetic coils, the screw and electrical contact separate and open the electric circuit powering the electromagnetic coils. Accordingly, the electromagnetic coils turn off, and the armature, which is spring-biased away from the electromagnetic coils, moves away from the electromagnetic coils and pulls the needle out of the skin. As the armature moves away, the screw and electrical contact touch, the electric circuit is closed, and the electromagnetic coils are reactivated. This process repeats as long as electricity is supplied to the contacts. Traditionally, the handle of an electromagnetic coil tattoo apparatus is placed on a needle tube in which the needle is placed whereas the electromagnetic coils and the reciprocating mechanism is placed above the handle.
- a rotary tattoo machine includes a motor spinning a cam wheel as an oscillating or reciprocating mechanism. The cam wheel includes an offset shaft that is offset from the rotational axis of motor by a distance. A first end of a needle is attached to the offset shaft, while the main shaft of the needle is received in a needle tube or otherwise fixed in at a lateral position. The second end of the needle oscillates back and forth through the skin surface. The stroke length of a rotary tattoo machine is primarily determined by the distance between the center of the cam wheel and the offset shaft, the stroke length may be reduced if the rotary tattoo apparatus is configured with a give-function such as a flexible part placed between the offset shaft and the needle. Traditionally, the handle of a rotary machine is placed on a needle tube in which the needle is placed whereas the motor and the reciprocating mechanism is placed above the handle.

US2017/0007814A discloses a tattooing apparatus having an automated control of penetration depths. The tattooing apparatus includes a needle having at least one tip and a needle drive mechanism configured to move the needle between a first position and the second position, in the first position the tip is located above the surface of a skin and in the second position the tip is located at a penetration depth underneath the skin surface. The needle is configured to deposit an ink between the skin surface and the penetration depth. The tattooing apparatus includes a sensor (210) located in the outer frame of the tattooing apparatus, which sensor scans the skin at the point where the tip of the needle penetrates the skin and the sensor is configured to provide an output in form of a feedback signal corresponding to a skin thickness characteristic, possibly the sensor utilizes optical coherence tomography (See [0029]) or ultra sound (See [0030]) to detect skin layer depths and thicknesses. The tattooing apparatus also includes a controller configured to receive the feedback signal from the sensor, the controller then determines the optimal penetration depth based on the skin thickness characteristic and then adjust the penetration depth (See [0028]). The needle penetration depth is adjusted during use such that ink is consistently deposited within a particular layer of skin. In a rotary tattoo apparatus, the needle penetration depth is adjusted by moving the motor and cam wheel vertically up and down in small increments relative to the needle tube or alternatively, the distance between the rotational axis and the offset shaft is adjusted or alternatively, the length of the needle tube is varied. In an electromagnetic coil machine, the needle penetration depths may be adjusted by varying the distance between a frame (302) to which the coils are attached and the needle tube (308) (See [0035]). If a linear electric motor is used for the tattooing apparatus, the stroke distance of the needle may be adjusted by controlling the actuation of the motor (See [0037]).

The tattooing apparatus of US2017/0007814A varies the end position of the stroke length as a function of the skin characteristics. For the rotary machine and the electromagnetic coil machine, the stroke length is kept constant while the distance between needle attachment and the handle of the apparatus is varied. In the FIGS. 2A and 3A of the document, the apparatuses are illustrated in a vertical position, it is not clear how the device will react if it is held in an 45°-angle relative to the skin surface.

Normally, the parameters a tattooist must set when using a traditional tattooing apparatus is the voltage of the motor, determining the frequency of the needle, and set the stroke length of the needle. Both parameters are normally set at the beginning of a tattoo session and may then be manually changed during a session. However, drastically changing give, or stroke length of the needle often requires replacing a mechanical part of the tattooing apparatus taking both time and effort. Also, mechanical give may be subject to wear and other conditions.

SUMMARY

The invention relates to an oscillation apparatus such as a tattooing apparatus applying an electric motor such as a linear electric motor. In the content of the present application, a linear electric motor is defined as a motor being able to move an element such as a needle or a connector for a needle back and forth along a straight line in an oscillating way, and the linear electric motor is able to accelerate, decelerate, change direction, start or stop and hold at any position or state of an oscillation.

Some traditional tattooing apparatus are considered to be driven by a linear electric motor, and some are not. A traditional rotary machine or tattoo apparatus is not driven by a linear electric motor as a spinning cam wheel is not viably able to stop and change direction, this motor must continue a full stroke and the full stroke may only be limited by including give-functionality in the needle.

A linear electric motor may consist of a flat magnetic core with transverse slots that are often straight cut with coils laid into the slots, each phase giving an alternating polarity so that the different phases physically overlap.

A voice coil motor is a linear motor and the term "voice coil motor" generally refers to a motor mechanism using a solenoid within a magnetic field to move an object back-and-forth. Linear DC Motors, Voice Coil Motors (VCM) or Voice Coil Actuators (VCA) are simple electric motors where the motor comprises two separate parts; a magnetic housing and a coil.

The purpose of the present invention is to obtain an oscillating apparatus such as a tattooing apparatus having optimized operating conditions, meaning that the user has more and better control over different aspects of the tattooing apparatus, and therefore the outcome of the tattoo itself.

Until now, such control of the tattooing apparatus parameters has not been possible, and the outcome of the different tattooing techniques had more to do with the skill of the tattoo-artist.

Traditionally, a tattooist will have to learn to handle a given tattooing apparatus to obtain a perfect result for a tattoo. When using a tattooing apparatus according to the present invention, a tattooist will be able to control the functions of the tattooing apparatus and therefore it will be possible to adapt the functionality of the tattooing apparatus to the skills and working methods of the tattooist.

Furthermore, since the tattooing apparatus is controllable and self-regulating, it will produce more consistent results than other tattooing apparatus, meaning, for example, that the tattooist who is less experienced will have to use less time to get to know the tattooing apparatus and will therefore be able to concentrate on his/hers own working techniques or art.

I.e. the tattooing apparatus supports the creation of perfect artwork by fully controlling the needle, making it possible to deposit an optimal amount of ink at an optimal depth, or to color larger areas of skin at a higher speed while still obtaining a perfect coloring. The perfect results may be achieved regardless of whether it relates to coloring of larger skin surfaces, to line drawing or to shading and they may be obtained for all known needle types.

The invention allows the user to specify a profile for a given tattoo-process and by specifying a profile, the tattooist may optimize the deposition of ink for this process whether the process is providing sharp lines, shadows or something else.

A profile may e.g. be specified in respect of movement type, frequency, stroke length, give/force and feedback control from sensor input, such as the accelerometer, etc.

"Movement type" is defined as a set of 2-dimensional points (x, y). The points (x, y) represent the relative position of the needle with respect to an internal timebase of the microcontroller (timebase, relative position). For example, the tattooing apparatus can be set to run a set of points that show a sine wave when plotted on a graph. The motor, and therefore the needle, will then attempt to move exactly as defined in the sine graph.

Other factors of the profile are for instance frequency, which governs the timebase, that is how often per second the tattooing apparatus cycles (usually one whole set of positioning points), and stroke length, governing the total length of the travel of the needle.

Frequency determines how often the needle cycles a full set of positioning points (one period) in one second, usually, how often the needle penetrates the skin surface and is a defining factor of the density of the ink dots i.e. the higher frequency the higher inkdot density.

The stroke length of the profile defines the planned stroke length i.e. the length the needle tip moves from a retracted position to a forward position, the stroke length may be reduced if the tattooist works with give.

"Give" is a special function in a tattooing apparatus, used to set the maximum force to be used when the needle pushes into the skin. "Give" is a legacy name originating from the use of spring loaded needles. The present invention allows the user to precisely set the give or force of the needle, by adjusting the working parameters of the electric motor. The give can be set as a constant or as a mathematical function of a variable (Algorithm). In effect, the give is a conditional variable that may reduce the total stroke length of the needle, if certain prescribed circumstances arise.

In general, a user may during a tattoo-session choose to add a "give" defining a maximum of force applied to push the needle into the skin, possibly while the tattoo apparatus is activated i.e. running, and/or a "give" may be included within a given profile, and/or a "give" may be made dependent on measured variables, i.e. the give is applied as a feedback control.

The amount of deposited ink is greatly influenced by the used needle type, however, choice and use of specific needle types are not within the aspects of the present invention according to which any kind of needles can be used.

When tattooing, an example of a general problem is how to increase the speed of the work without compromising an optimized deposition of ink. The present invention makes it possible to increase effectiveness, and therefore speed, in the tattooing process as the travel distance of the needle and the velocity at which the needle travels between a first position above a skin surface and a second position at a penetration depth below the skin surface may be optimized at any position of the needle.

This ability makes it possible to increase the effectiveness of the deposition of ink into the skin, by controlling the movement of the needle. As an example, it may be advantageous to insert the needle fast or slow into the skin, then wait for a few milliseconds, and then retract the needle slow or fast from the surface of the skin. When gaining experience, a tattooist will be able to better understand the mechanics of the tattooing process and will be able to customize the movements of the needle to best fit the work at hand by making his or her own movement types defined by sets of 2-dimensional points (x, y).

The movement or travel of the needle may also be chosen to gain different effects e.g. relating to work-time and or different tattooing techniques. As an example, the frequency of the needle may be increased if the tattooist suddenly moves the needle faster along the surface of the skin. That is, to keep up a similar number of needle-hits per length, the tattooing apparatus may be provided with an accelerometer to sense the movement and adjust the frequency to compensate if needed.

This ability makes it possible to reduce the time periods where the needle is not engaged in deposition of ink but only travels to re-arrange for a new insertion and corresponding deposition of ink, i.e. the time the tip of the needle spends above the skin surface may therefore be as short as possible.

When a tattooist moves a tattooing apparatus too quickly across the skin, the needle will cut sideways into the skin instead of delivering a dot of ink. This means that the skin becomes traumatized, the risk of infection increases and the colored skin cures poorly. For optimal color intensity, it is important that the ink is delivered in the right skin layer with a precise dot. If the needle moves too fast along the skin's surface compared to how fast the tattooing apparatus works, one will see redness and increased bleeding, where the skin has been cut/ripped by the needle, the skin will heal slower and the color will worsen over time.

Due to other considerations and working routines, tattooists may prefer different velocity patterns for a profile, if e.g. a tattooist wishes to swipe fast over the skin surface, it is desirable that the needle spends as little time as possible below the skin surface and it is then advantageous if the needle is inserted through the skin surface to the full penetration depth at a high velocity and also retracted from the skin surface at a high velocity with no waiting in between.

A feedback control of the needle position will continuously strive to achieve that a desired behavior for the needle is maintained. As the structure and thickness of the skin surface varies, the motor of the apparatus will need to vary the force with which the needle is inserted to overcome this variation and follow the desired profile. A desired profile will act as a feed forward control of the needle position whereas the variation of skin structure and thickness will cause a disturbance which a feedback control may help to overcome.

A problem often experienced during tattooing is that the skin surface bounces up and down because the skin is both elastic and influenced by the needle moving back and forth at a high speed during tattooing. As a result, the actual insertion depth of the needle not only depends on the pre-setting of the tattooing apparatus, it also depends on the current position of the skin surface. When the skin bounces up and down, ink may be deposited at too high a level i.e. in the epidermis, causing the ink to leave the skin through keratinization resulting in a detrimental effect on the tattoo or ink may be deposited to deep causing lines and edges to be blurred as the color diffuses through the blood carrying layers causing the skin surface to be unevenly colored (Mexican shading), Depositing the ink to deep may also result in increased health risks as this allows ink and microorganisms into the blood carrying layers.

Beyond providing poor coloring of the skin surface, the bouncing up and down of the skin surface may also cause discomfort to the tattooee as the needle may not be completely retracted from the skin surface at the speed used by the tattooist when moving the needle along the skin surface. This will cause more trauma to the skin of the tattooee than necessary.

The above problems are solved by applying an oscillating apparatus according to claim 1.

An oscillating apparatus such as a tattooing apparatus according to the invention comprising a housing, a handle, a power supply and a needle connector configured to be coupled or connected or attached or fixed to a needle having at least one needle tip, said needle connector is configured to move relative to a stationary part of a linear electric motor, the needle connector being configured to move reciprocating along a line between a retracted position and a forward position;

a linear electric motor having a variable and controllable motor controlling stroke length, position and velocity of the needle connector;

which apparatus further comprises a first sensor and a controller, wherein the first sensor is configured to read the linear position of the needle connector and transmit the reading as an input to the controller, and the controller is provided with a profile for the linear position of the needle connector and is configured to receive the input from the first sensor, compare the input from the first sensor with the profile for the linear position of the needle connector and send an output to the linear electric motor correcting the stroke length and velocity of the needle connector to adapt to the profile for the linear position of the needle connector.

The profile may define a movement type (x, y) of the needle relative to the stationary part of the linear electric motor. The profile may also include information relating to frequency, stroke length and other variable parameters influencing the result of a tattooing operation.

The movement of the needle is defined relative to the stationary part of a linear electric motor positioned in the housing of the tattooing apparatus, the tattooing apparatus as such, i.e. including the linear electric motor and the needle, may further be moved relative to a skin surface, and relative to the skin surface the tattooing apparatus as such may have a velocity and an acceleration defined by the tattooist.

According to one or more embodiments of the invention, the needle connector is attached either releasably or unreleasably to the needle by a rigid connection i.e. the attachment of the needle connector to the needle is not elastic and does not introduce or add elasticity in the transfer of movement from the needle connector to the needle. I.e. when the needle is attached to the needle connector the combined needle and needle connector may be considered to be a single system moving together as one.

According to one or more embodiments of the invention, the apparatus may comprise a second sensor or a second and a third sensor which sensors or sensor may either be configured to measure the current or the change in current in the linear electric motor or configured to measure acceleration of the tattooing apparatus relative to a skin surface in one or more axes.

According to one or more embodiments of the invention, the linear electric motor may be a voice coil motor or a linear multi-phase motor or the like.

According to one or more embodiments of the invention, the handle may be positioned in such a way that the handle encircles at least a part of the linear electric motor, i.e. the handle is not positioned in extension of or as an appendix to the linear electric motor and thereby a shorter and/or more compact unit can be provided.

According to one or more embodiments of the invention, the apparatus may comprise means to vary "give" while the linear electric motor is activated i.e. running.

According to one or more embodiments of the invention, the controller or part of the controller may be placed outside the housing, in its own enclosure, perhaps with the power supply, and connected via a wire or radio waves to the controller.

According to one or more embodiments of the invention, a coupling part (10) may be releasably or unreleasably attached to the oscillating apparatus, the coupling part (10) may comprise means corresponding to respectively the needle (11) and to oscillating apparatus e.g. the housing (8) of the oscillating apparatus which means are configured to keep the coupling part (10) stationary relative to the housing (8) and relative to the needle (11).

According to one or more embodiments of the invention, the coupling part (10) may comprise a light source, the light source may be positioned at or around the perimeter of the coupling part (10) at a surface facing the needle (11), and the light source may either be distributed evenly around the circumference of the surface facing the needle (11) or the light source may be positioned as one or two or three or four or more positions at the surface facing the needle.

Tattoos are pieces of art that rely on different colors and shadows and they are therefore subject to light. It is important that an artist is able to compare his/her work to the right type of light for reference an it is therefore advantageous to have a work light placed into the apparatus itself. The work light can be adjusted according to light intensity and color. When the same setting is used constantly, the artist (especially travelling artists) can have a known light source.

Optionally, the light source may be governed by the movement of the machine, so that the artist may choose to block out the light that does not fall onto the skin of the customer.

According to any embodiment of the invention, a motor-rod forming the needle connector (2) may be rigidly coupled or attached to the needle (11) during operation transferring all movements of the motor-rod to the needle (11). Normally, a needle or needle system is releasably coupled to the needle connector or apparatus thereby allowing replacing of the needle.

According to any embodiment of the invention, the controller may comprise means for identifying the needle (11) or needle type, e.g. by reading a code or by identifying travel length or other physical characteristics, and then the controller may be configured to select a profile, or a group of profiles, based on the identification of the needle or needle type The invention also relates to a method for controlling an oscillating apparatus such as a tattooing apparatus comprising a needle and/or a needle connector and a linear electric motor and a controller controlling position, velocity and acceleration of the needle and/or the needle connector; the method comprising providing a controller with a profile for the linear position of the needle connector in form of a function $y=f(t)$ defining the position and the velocity of the needle y relative to a stationary part of the linear electric motor over a period $T_n$, the period $T_n$ being repeated n times where n is determined by the length of the tattoo session;

measuring the position of the needle connector $y_m$ at time t relative to a stationary part of the linear electric motor and providing this position $y_m$ as input to the controller, then the controller compares the input value $y_m$ to the reference value provided by the function $y=f(t)$ and based on the error calculated from the reference values $y=f(t)$ and the measured value $y_m$, the controller transmits an output to the linear electric motor, thereby correcting position with respect to time.

By this function the position of the needle connector or the movements of the needle connector or the force to the linear electric motor may be corrected.

According to one or more embodiments of the invention, the current consumed by the linear electric motor may be measured by a current sensor, and then the value for the consumed current may be provided as an input to the controller and/or the acceleration of the apparatus in one or more axis may be measured by an acceleration sensor and then the value for the acceleration may be provided as a vector quantity for each axis as an input to the controller.

According to one or more embodiments of the invention, the measurement of the current to the controller may be used to optimize the behavior such as the frequency or the force of the linear electric motor and/or measuring of the apparatus' acceleration may be used to calculate speed and travel of the tattooing apparatus relative to the surroundings.

According to one or more embodiments of the invention, the needle connector may be moving forward at one velocity or one velocity movement type and backward at a different velocity or a different velocity movement type, i.e. $v_f(t) \neq v_b(t)$, and normally $v_f(t) < v_b(t)$, where the forward direction is a direction from a retracted position towards a forward position at which forward position the needle connector during operation will obtain its penetration depth.

As a vector representing the velocity always will be pointing in the opposite direction when moving forward compared to when moving backward, the above differences for the velocity also refers to the absolute values of the velocity: $\|v_f(t)\| \neq |v_b(t)|$, and normally $|v_f(t)| < |v_b(t)|$. However, the expression also refers to that the needle connector may not move along a regular sine curve where the forward and backward movements or graphs are mirrors around a vertical axis, the needle may be moved according to different pattern where the forward and backward movements or graphs are not mirrors around a vertical axis.

DEFINITION OF WORDS

Ink: liquid to be or being deposited in a subject's skin during tattooing providing a permanent coloring of the skin Tattooist: a subject performing tattooing i.e. a subject operating the tattooing apparatus Tattooee: a subject being tattooed i.e. having ink deposited in a skin surface Linear position: is the actual position of the needle defined by a value for a distance e.g. measured from the fully retracted position where the fully retracted position then has the value 0. The value may also be defined as a percentage.

A linear electric motor: is a motor able to move an element such as a needle or a connector for a needle back and forth along a straight line in an oscillating way, a linear electric motor is able to accelerate, decelerate, change direction, start or stop and hold at any position or state of an oscillation depending on input from a controller.

Profile: A profile defines a set of variables which variables define a tattooing process such as position as a function of time, frequency, travel length/stroke length, "give" etc.

Needle: in the context of the present application the word "needle" normally refers to a needle system which at one end comprises a single needle tip or a plurality of needle tips and at the other end comprises means to attach the needle or needle system to an oscillating apparatus such as a tattooing apparatus. Normally, needles used for tattooing are not hollow.

Controller: may be a microprocessor and is a component that performs instructions and tasks involved in control processes, the controller is a unit that executes and manages the logical instructions passed to it.

In general: These words indicate that the features specified after the words may be applied to all embodiments of the invention although the features are not specified in the general part of the description.

DETAILED DESCRIPTION OF THE INVENTION

Figure 1:
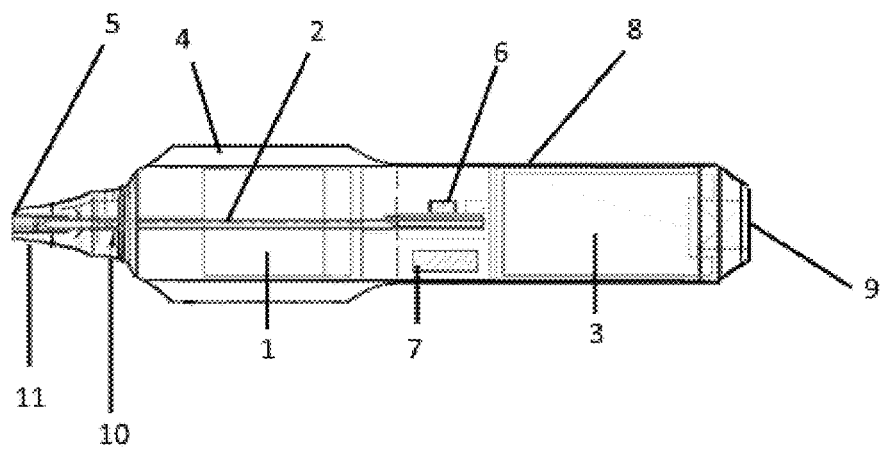
FIG. 1 shows an embodiment of an oscillating apparatus such as a tattooing apparatus according to the invention.

FIG. 1 shows an embodiment of an oscillating apparatus such as a tattooing apparatus provided with an oscillating or a reciprocating part according to the invention. The apparatus comprises a linear electric motor 1 and a needle connector 2 which needle connector 2 is in rigid i.e. non-elastic contact with a needle 11 during operation, that the two parts are in rigid contact means that the two parts move together and that movements of the needle connector 2 also defines movements of the needle 11. The needle 11 comprises a needle tip 5 which is able to penetrate a skin-surface. The linear electric motor 1 is provided with a power supply which may be a battery 3 as shown in FIG. 1 or a cord connected to a power source. Also, the apparatus comprises a position sensor 6 a controller 7. The apparatus is further provided with a handle or grip 4 where the tattooist holds the apparatus during tattooing and a housing 8 providing an outer shell within which all the functional parts of the apparatus i.e. the linear electric motor 1, part of the needle connector 2, the position sensor 6 and the controller 7 may be enclosed. The apparatus also comprises activations means which in the embodiment of FIG. 1 is provided as an end-positioned on-off button 9.

The embodiment shown in FIG. 1 comprises a coupling part 10 and a needle 11 where the coupling part 10 is positioned between the needle 11 and the oscillating apparatus.

In general, the coupling part 10 is optional. The coupling part 10 may add further features to the oscillating apparatus such as a light source or the coupling part 10 may be configured as an adaptor allowing use of needles developed for other apparatuses together with an oscillating apparatus according to the invention.

The needle 11 comprises a first end provided with a plurality of pointy or sharp tips 5 able to cut through a skin-surface and an opposite second end comprising means to attaching the needle 11 to the oscillating apparatus. The needle 11 may comprise attachment means corresponding to attachment means of the oscillating apparatus, and the needle 11 may then be directly attached to the oscillating apparatus. Alternatively, the needle 11 may comprise attachment means corresponding to the attachment means of the coupling part 10, and the needle 11 may then be attached to the coupling part 10 which coupling part 10 is then attached to the oscillating apparatus, the needle 11 is then indirectly attached to the oscillating apparatus.

The coupling part 10 comprises attachment means for both the needle 11 and for the oscillating apparatus. The attachment means of the coupling part 10 may correspond to means of the housing 8, and the attachment means may comprise corresponding threads or click-parts or the like.

If an apparatus according to the invention has been configured with a cord connected to a power source, activation means may be provided at the distant power source.

In general, a tattooing apparatus according to the invention may also be provided with a current sensor for regulating current in the coil which may be positioned between the motor and an amplifier driving the motor, however, a current sensor is not shown on the figure. Further, the apparatus may comprise an accelerometer. Also, an apparatus may comprise a secondary motor with a secondary position sensor, the purpose of the secondary motor being to regulate unwanted forces being generated by the primary motor.

The needle 11 may be of any type such as round tattoo needles, flat tattoo needles, magnum tattoo needles such as weaved, stacked, round, curved or bugpins. An apparatus according to the invention may have a system for coupling the needle onto the apparatus and/or onto the needle connector. The coupling may comprise or be constituted of corresponding parts on the needle and the apparatus/needle connector and the coupling may be implemented as a twist and click collar, snap on, or screwed when positioning and attaching the needle relative to the apparatus.

Most, or perhaps all, prior art cartridge-using apparatus' do not have an actual coupling mechanism to a needle. Instead, prior art cartridge machines rely on a certain spring force to hold the needle against the actuating rod. As a consequence, the prior art apparatus' do not pull the needle back into the cartridge, they only push the needle forward, so the needle penetrates the skin, and let the cartridge pull the needle back. That is accomplished with the help of a membrane, acting as a spring, which membrane is attached between the cartridge and the needle itself. The present invention does not rely on such a spring mechanism, instead the motor-rod forming the needle connector 2 may be directly attached to the needle 11 during operation by a non-elastic coupling, so that the needle is hard-coupled to the motor. The needle 11 will therefore act out any movement initiated by the motor.

In general, a linear electrical motor comprising a moving member arranged to reciprocate within an opening in, or defined by material of, a stationary member may be used in the construction of the apparatus according to the invention. Such a motor is shown in FIG. 1. Such motors are known and are considered available shelve products i.e. the motor is not inventive as such.

The linear electric motor used to construct an apparatus according to the invention is able to position the needle at a preferred position with a given velocity and acceleration. Examples of a motor able to perform this way is a voice coil motor or a multi-phase linear electric motor.

In the embodiment of FIG. 1, the needle connector 2 is placed centrally through the linear electric motor 1, i.e. the needle connector 2 is connected directly to and moves simultaneously with the reciprocating moving part of the linear electric motor 1. Alternative positions of the needle connector 2 may be possible; however, the central position provides a good balance for the apparatus during tattooing. Also, according to the embodiment of FIG. 1 the handle 4 is surrounding the linear electric motor 1 providing an improved distribution of the weight of the apparatus during tattooing as the significant weight of the motor is positioned close to the needle tip 5.

First Sensor:

In general, the first sensor 6 is a position sensor configured to measure or read the position of the needle connector 2 or a part directly connected with the needle connector 2 making it possible to establish the exact position of the needle connector 2, the needle 11 and the needle tip 5 at a specific time or at all times. Such sensors are known and are considered available shelve products i.e. the sensor is not inventive as such. Further, the first sensor 6 is configured to transmit obtained data relating to the position of the needle connector 2 to the controller 7.

The first sensor 6 is normally placed inside the housing and it may function and may be a magnetic incremental sensor, i.e. it measures changes in the magnetic field of a stripe sitting below the sensor. Alternatively, an optical sensor may be used, such an optical sensor measures light intensity from a light source opposite the sensor. When a gear-tooth in a motor intercepts the beam, then the sensor measures the dimming in the light and then determine that there was a movement.

Using more than one position sensor or position sensing elements, angularly offset from each other, it is possible to measure not only speed of movement but also direction. This type of sensor can only be used to determine distance from first position measurement to current position. Therefore, the tattooing apparatus will have a "Find zero position-function", for when it is turned ON from an OFF mode. Or when the controller finds that the true position has been lost perhaps due to a "knock" on the tattooing apparatus or the controller finding end-of-travel points of the motor/needle. This type of sensor only counts number of steps in one direction.

A sensor may have a third counting phase that can be used to determine if known travel length has been lost. The counting distance for the third phase may be much longer, about one count per 2 mm, but can be used to regain the position without using a Find-zero function.

Another type of sensor that can be used is an absolute position sensor. This type of sensor only looks on "a measuring stick" and reads its current position. Pricing and performance are factors to be considered when choosing the right sensor for the design.

The Controller:

In general, the controller 5 may be a microprocessor which is configured with a profile indicating e.g. the desired position of the needle during tattooing. The profile may function as a set point for the controller 5, and the controller 5 is configured to transmit an input to the linear electric motor 1 making the linear electric motor 1 drive the needle connector 2 according to the profile.

As the needle connector 2 only moves along a single axis relative to the housing 8 and relative to the stationary part of the linear electric motor 1, the position y of the needle connector 2 can be defined as a function of one variable t (time): $y=f(t)$ and may be illustrated in graphs as shown in FIGS. 2A and 2B.

Figure 2A:
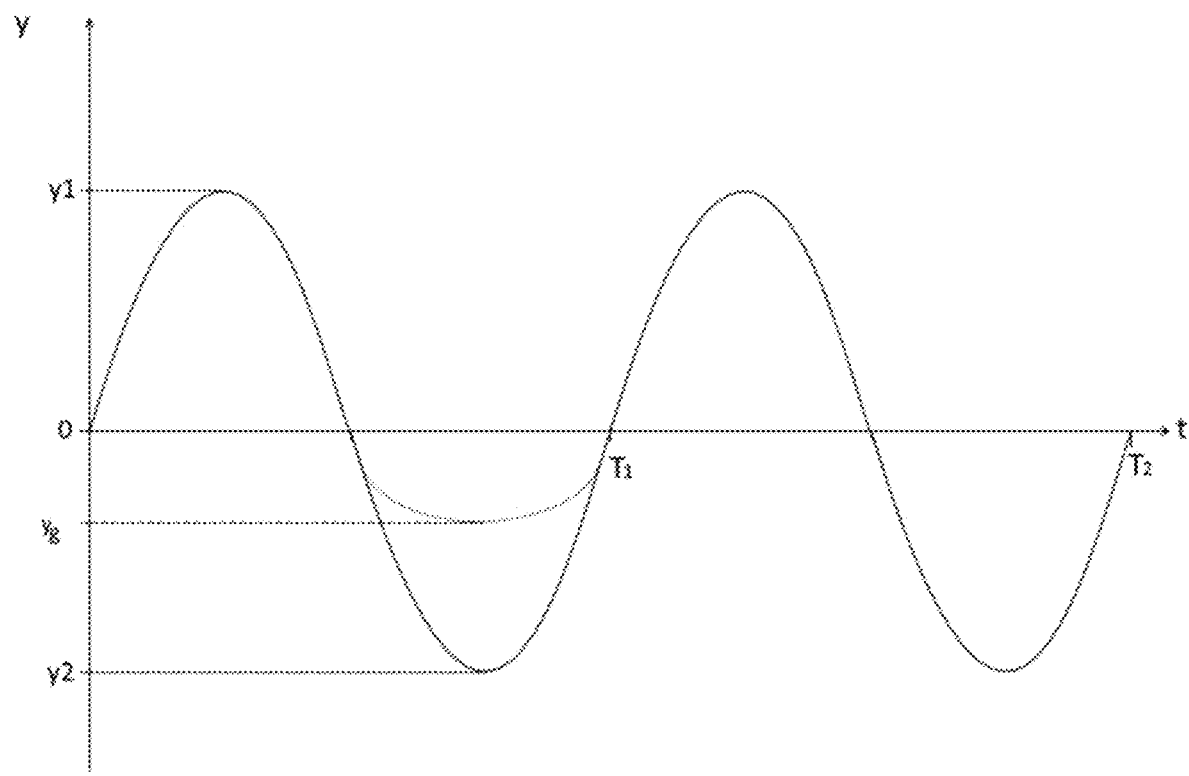
FIGS. 2A and 2B shows examples of a profile for the linear position of the needle working as set points for the controller.
Figure 2B:
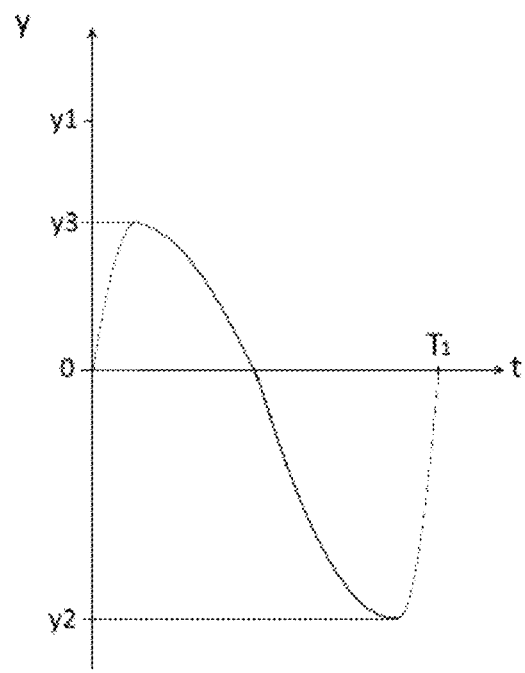

FIG. 2A shows an example of a profile according to which the needle connector 2 and the needle 11 moves like a pendulum with a period T and FIG. 2A illustrates two consecutive periods $T_1$ and $T_2$.

The complete stroke length according to the profile is $y_1+y_2$, where $y=0$ indicates the skin surface if the tattooing apparatus is placed in an angle perpendicular to the skin surface, and the needle tip 5 will normally have a penetration depth of $y_2$. This profile is similar to the needle-movements obtained by traditional tattooing apparatuses such as a rotary tattoo apparatus.

A give reduces the maximum penetration depth to $y_g$ regardless of the desired position and the inputs to the controller, if the give is not added the needle will—regardless of the physical circumstances—attempt to punch through to the profile defined penetration depth and this may traumatize the skin surface. If the give is added the complete stroke length will be reduced to $y_1+y_g$ during tattooing. If the needle meets no resistance e.g. if the tattooing apparatus is run in free air, the give will not have any effect. In an apparatus according to the invention, the give is set by controlling the current through the linear electric motor and thus the user will be able to set and fine tune the give while the apparatus is running.

FIG. 2B shows another example of a profile where the needle 11 will cut through the skin surface and move through the skin at the same velocity as the indicated in the profile of FIG. 2A, i.e. from $y=0$ to $y=y_2$ the profile is the same. According to the profile of FIG. 2B the retraction velocity of the needle has been increased i.e. the total time of a period T has decreased and the stroke length of the needle has also decreased and is according to the profile of FIG. $2B=y_3+y_2$ $(<y_1+y_2)$.

A given profile may be chosen by a user depending on what kind of coloring the user is going to apply e.g. whether it is line-drawing or shading, and what kind of needle type the user is going to use. In fact, the profile is the desired settings of all the variables which the tattooing apparatus controls. When these settings are saved to be recalled back later, it is called a profile. The main purpose of the profile is for the user to recall the setting last used for a specific task or specific needle, skin type, effect, etc.

An apparatus according to the invention may include a current sensor, used to measure the current in the motor for several purposes. Firstly, the current may be used to measure how much energy is put through the motor. This will support maintaining good regulation of the moving parts and the forces doing the work. Secondly, the current sensor is relevant for the give function. Since the force of the motor may be controlled by regulating electrical current running through its coils, using a current sensor is a very useful method of determining the amount of force used by the motor to move, or penetrate the skin. If desired, the tattooist may choose to set an upper threshold of the current used to penetrate the skin. Such a force-restraint is normally called give.

A problem often experienced by tattooists is movement of the skin-surface caused by the reciprocating needle's contact with the skin. As the skin is flexible the reciprocating needle makes the skin bounce up and down and because of this wave behaviour the distance between the needle tip 5 and skin is constantly changing, sometimes the skin is close and sometimes it is farther away. As an effect, the needle's penetrating depth is constantly changing. This has a detrimental effect on the quality of the tattoo.

Also at a certain frequency this effect becomes a standing wave, this frequency is different from area to area and is higher where the skin is tighter. This is called resonance and results in a longer travel of the skin. One aspect of the present invention is to solve the problem arising when the needle causes resonant waves on the surface of the skin. Resonant bouncing of the skin causes excessive changes in the needle's penetrating depth, which is greatly affected by changes in phase between skin movement and needle movement. This may be solved by activating what is called an anti resonance function. Because the resonant frequency is a very narrow band, it is possible to constantly vary the frequency of the needle movement to counter the effect. For example, a tattooist sets the desired frequency to 50 Hz, then the tattooist activates the anti-resonance function, which constantly varies the operating frequency around the set frequency, e.g. from 45 Hz to 55 Hz. This method will not detect a resonant wave but prevents the resonant wave from becoming a problem by never staying at longer periods of time at the resonant frequency should it be a close numerical value to the user selected operating frequency (50 Hz in the example above).

In general, a tattooing apparatus may also comprise a further sensor in form of an accelerometer, which sensor measures acceleration in one or more axes. Conceptually, the sensor functions by measuring a mass suspended in free air with springs, when the frame of the sensor is moved the inertia of the mass causes the springs to stretch. An accelerometer sitting on a table will show a force of 1G acting upwards due to the gravity of the earth. Rotational forces may also be measured with an accelerometer. A multi axis accelerometer is often referred to as an IMU (Inertial Measurement Unit).

Normally such sensors are micromachined, and often piezo crystals are used as the sensing element, but other types of sensors may also be used.

The output from an accelerometer is usually a vector quantity for each axis, that is both the direction and size of the force acting on the sensor itself making it possible to calculate speed and travel as well, by means of mathematical integration.

It should be understood that by using a multiaxis IMU, it is possible for an apparatus to know where it is within its own or a provided frame of reference.

There may be several reasons for adding an acceleration sensor to the apparatus:

1) The tattooing apparatus can interpret the users gestures. This allows the user to communicate with the tattooing apparatus, fx if the user wants to turn on/off a certain function, such as the anti resonance-function, the user might only have to make a waving gesture to accomplish this. This feature results in a reduced risk of contamination as the user does not have to touch anything but the tattooing apparatus. The tattooing apparatus will need less or no buttons/electrical contacts, and as a result there are less possibilities for moisture or chemicals to enter the tattooing apparatus.

2) The tattooing apparatus can sense its own movements/or lack thereof, meaning that if is is dropped then it can turn itself off before landing on the floor, with the needle retracted and motor in a safe state. Or if it is simply put down to rest, the tattooing apparatus can be set to stop moving/turn off.

3) The tattooing apparatus can adapt itself to the artist, the movements of the tattooing apparatus can be set to have an effect on one or more variables. As an example, when the "drawing-speed" of the tattooists hand changes, then changes may be made to the frequency of the needle, keeping the ratio of needlehits per length of line more constant.

4) Regulation of unwanted movement of the tattooing apparatus due to motor/mass movement.

Further, the data from an accelerometer can be used to minimize the shaking of the tattooing apparatus experienced during a work session, reducing fatigue of the tattooist.

The amount of power going into the motor may be controlled by Pulse Width Modulation (PWM). According to this method pulses are used to turn the output stage fully ON or fully OFF at a fast rate. The timeperiod of each pulse is always the same, hence the frequency is kept constant, however, each pulse is divided into two sub-periods, one where the pulse is high and the amplifier transfers voltage to the motor (ON), the other where the puls is low (OFF) and the amplifier does not provide voltage to the motor. This method has been used to dim the light in a livingroom, provided that the switching is done fast enough the human eye will not experience fluctuating of the lightsource.

The motor will also only register the mean value of power provided by the amplifier.

The ratio between the ON and OFF periods is called duty cycle. A 50% duty cycle means that the ON and OFF periods are of the same length. A 10% duty cycle means that the pulse is only ON for 10% of the total period. Or 10% of the total time, meaning that only 10% of available power is supplied to the motor (See FIG. 3).

Figure 3:
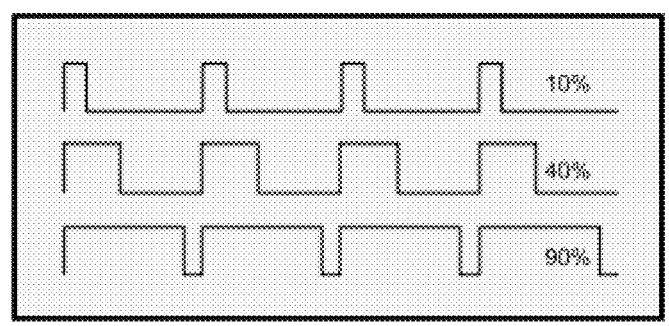
FIG. 3 shows a three different duty cycles for a motor controlled by Pulse Width Modulation (PWM).

FIG. 3 shows a changing square wave representing the PWM pulses being fed from the amplifier to the motor.

The sinus wave represents the power output from the amplifier or the movements of the motor, back and forth.

The output of the amplifier may be smoothed out using fx a low pass filter, this is not allways necessary since a motor has both electrical and mechanical inertia that will smooth out the movements of the motor.

A variant of this invention is a tattooing apparatus that uses a secondary motor, to counteract or neutralize the detrimental effects of the primary motor accelerating back and forth.

Since the primary motor has a specific mass, and is oscillating back and forth, and every action has an equal and opposite reaction, this will induce a shaking of the tattooing apparatus.

The same type of motor, or similar, can be made to move the exact opposite way of the primary motor, and again according to Newtons law, this will prevent the user from experiencing the shaking of the tattooing apparatus. That is if the masses and accelerations are equated. Here the accelerometer also comes in handy as it can be used to feedback an error signal to the controller, which in turn adjusts the movement of the secondary motor accordingly. The error signal would then be caused in the first place by mismatch of the forces of the two motors, then to be adjusted as not so.

In general, to ease the process of changing a needle and then select a matching profile for a certain task, the apparatus may comprise means for recognizing that the needle 11 has been changed. This might be implemented by any of several means.

As an example, after the needle has been mechanically attached to the apparatus, the apparatus might investigate the needles allowed/possible travel. By making needles having different travel lengths, it is possible to "encode" the name and/or type of needle into a lookup-table, and match a movement profile with a certain needle. Then the apparatus may be set to automatically change to the required profile after sensing a different type of needle.

Other methods of needle identification could be, sensors that can identify colour coding on a part of the needle that sits inside the apparatus, or light admittance (barcodes), or mechanically actuated switches e.g. the needle having a collar or a mechanical construction that mechanically activates different switches, or magnetic sensors, polarity, field strength, etc. by placing magnets/magnetic materials into the needle.

| Ref. no. | Name |
| --- | --- |
| 1 | Linear electric motor |
| 2 | Needle or needle system connector |

-continued

| Ref. no. | Name |
|---|---|
| 3 | Power supply |
| 4 | Handle |
| 5 | Needle tip |
| 6 | First sensor |
| 7 | Controller |
| 8 | Housing |
| 9 | On-off button |
| 10 | Coupling part |
| 11 | Needle or needle system |

The invention claimed is:

1. An oscillating apparatus such as a tattooing apparatus comprising:
a housing, a handle, and a power supply;
a needle connector configured to be connected or attached or fixed to a needle having at least one needle tip, the needle connector being configured to move relative to a stationary part of a linear electric motor, and the needle connector being configured to move reciprocating along a straight line between a retracted position and a forward position;
a linear electric motor having a variable and controllable motor controlling stroke length, position and velocity of the needle connector;
the apparatus further comprises a first sensor and a controller;
wherein the first sensor is configured to read the linear position of the needle connector, and transmit the reading as an input to the controller, and
the controller is provided with a profile for the linear position of the needle connector and is configured to:
receive the input from the first sensor; compare the input from the first sensor with the profile for the linear position of the needle connector; and
send an output to the linear electric motor correcting the stroke length and velocity of the needle connector to adapt to the profile for the linear position of the needle connector.

2. The apparatus according to claim 1, wherein the apparatus comprises a second sensor or a second and a third sensor which sensors or sensor is configured to measure the current or the change in current in the linear electronic motor, or is configured to measure acceleration of the tattooing apparatus relative to a skin surface in one or more axes.

3. The apparatus according to claim 1, wherein the linear electric motor is a voice coil motor or a linear multi-phase motor.

4. The apparatus according to claim 1, wherein the handle is positioned in such a way that the handle encircles at least a part of the linear electric motor.

5. The apparatus according to claim 1, wherein the apparatus comprises means to vary give while the linear electric motor is activated.

6. The apparatus according to claim 1, wherein the controller or part of the controller is placed outside the housing, in its own enclosure with the power supply, and connected via a wire or radio waves to the controller.

7. The apparatus according to claim 1, wherein a coupling part is releasably or unreleasably attached to the oscillating apparatus, the coupling part comprising means corresponding to respectively the needle and to the housing of the oscillating apparatus which means are configured to keep the coupling part stationary relative to the housing and relative to the needle.

8. The apparatus according to claim 7, wherein the coupling part comprises a light source, the light source is positioned at or around the perimeter of the coupling part at a surface facing the needle, and the light source may either be distributed evenly around the circumference of the surface facing the needle or the light source may be positioned as one or two or three or four or more positions at the surface facing the needle, and may optionally be set to be influenced by a sensor causing to light to always be directed to the skin surface.

9. A method for controlling an oscillating apparatus such as a tattooing apparatus comprising a needle and/or a needle connector and a linear electric motor and a controller controlling position, velocity and acceleration of the needle or needle connector, the method comprising:
providing a controller comprising a profile for the linear position of the needle connector in form of a function $y=f(t)$ defining the position and the velocity of the needle or needle connector y relative to a stationary part of the linear electric motor over a period $T_n$, the period $T_n$ being repeated n times where n is determined by the length of the tattoo session;
measuring the position of the needle or needle connector $y_m$ at time t relative to a stationary part of the linear electric motor and providing this position $y_m$ as input to the controller, the controller comparing the input value $y_m$ to the reference value provided by the function $y=f(t)$ and based on the error calculated from the reference values $y=f(t)$ and the measured value $y_m$, the controller transmitting an output to the linear electric motor defining the variable motor parameters.

10. The method according to claim 9, wherein the current consumed by the linear electric motor is measured by a current sensor and the value for the consumed current is provided as an input to the controller, and/or the acceleration in one or more axes is measured by an acceleration sensor providing a vector quantity for each axis as an input to the controller.

11. The method according to claim 10, wherein the measurement of the current to the linear electric motor is used to optimize the behavior such as a force of the linear electric motor, and/or measurement of the acceleration is used to calculate speed and travel of the tattooing apparatus relative to the surroundings.

12. The method according to claim 9, wherein the needle or needle connector movies forward at one velocity or one velocity movement type and backward at a different velocity or a different velocity movement type in accordance with $v_f(t) \neq v_b(t)$, and normally $v_f(t) < v_b(t)$, where the forward direction is a direction from a retracted position towards a forward position where the needle connector during operation obtains its penetration depth.

13. The apparatus according to claim 1, wherein a motor-rod forming the needle connector is rigidly coupled to the needle during operation, transferring all movements of the motor-rod to the needle.

14. The apparatus according to claim 1, wherein the controller comprises means for identifying the needle or needle type by reading a code or by identifying physical characteristics, and the controller is configured to select a profile or a group of profiles based on the identification of the needle or needle type.

15. The method according to claim 9, wherein a motor-rod forming the needle connector is rigidly coupled to the needle during operation, transferring all movements of the motor-rod to the needle.

16. The method according to claim 9, wherein the controller comprises means for identifying the needle or needle type by reading a code or by identifying physical characteristics, and the controller is configured to select a profile or a group of profiles based on the identification of the needle or needle type.

* * * * *